United States Patent
Thekadath et al.

(10) Patent No.: US 11,777,730 B2
(45) Date of Patent: *Oct. 3, 2023

(54) LAYERED RECORDING NETWORKS

(71) Applicant: Visa International Service Association, San Francisco, CA (US)

(72) Inventors: Ajith Thekadath, San Ramon, CA (US); Sukrit Handa, San Mateo, CA (US); Suman Mukherjee, Foster City, CA (US)

(73) Assignee: Visa International Service Association, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/709,355

(22) Filed: Mar. 30, 2022

(65) Prior Publication Data

US 2022/0224533 A1    Jul. 14, 2022

Related U.S. Application Data

(63) Continuation of application No. 16/630,838, filed as application No. PCT/US2018/048173 on Aug. 27, 2018, now Pat. No. 11,323,258.

(Continued)

(51) Int. Cl.
*H04L 9/30* (2006.01)
*H04L 9/08* (2006.01)
(Continued)

(52) U.S. Cl.
CPC ............. *H04L 9/30* (2013.01); *G16H 10/60* (2018.01); *H04L 9/088* (2013.01); *H04L 9/3247* (2013.01)

(58) Field of Classification Search
CPC ........ G16H 10/60; G16H 40/20; G16H 80/00; G16H 40/67; H04L 9/30; H04L 9/3239; H04L 9/3247; H04L 9/088

See application file for complete search history.

(56) References Cited

U.S. PATENT DOCUMENTS 11,323,258 B2 * 5/2022 Thekadath ............. G16H 80/00
11,538,003 B2 * 12/2022 Moir ....................... G06F 16/27
(Continued)

FOREIGN PATENT DOCUMENTS

CN          101272330          9/2008
CN          102273143          12/2011
(Continued)

OTHER PUBLICATIONS

PCT/US2018/048173, "International Search Report and Written Opinion Received", dated Dec. 14, 2018, 13 pages.
(Continued)

*Primary Examiner* — Mohammad A Siddiqi
(74) *Attorney, Agent, or Firm* — Kilpatrick Townsend & Stockton LLP

(57) ABSTRACT

A method for providing interactive recording networks is disclosed. Multiple child networks can be established, each child network being coordinated by a respective coordinating entity. Each coordinating entity can also participate in a central parent network. A data package can be sent from one network to another. When a data package is sent to another network, additional data can be added to indicate that the data package is being escalated.

16 Claims, 10 Drawing Sheets

Related U.S. Application Data

(60) Provisional application No. 62/551,013, filed on Aug. 28, 2017.

(51) Int. Cl.
*H04L 9/32* (2006.01)
*G16H 10/60* (2018.01)

(56) References Cited

U.S. PATENT DOCUMENTS

| | | | |
|---|---|---|---|
| 2015/0332395 A1* | 11/2015 | Walker | G06Q 20/06 705/69 |
| 2016/0098723 A1 | 4/2016 | Feeney | |
| 2016/0292672 A1 | 10/2016 | Fay et al. | |
| 2016/0342989 A1 | 11/2016 | Davis | |
| 2017/0046651 A1 | 2/2017 | Lin et al. | |
| 2017/0048216 A1 | 2/2017 | Chow et al. | |
| 2017/0221288 A1 | 8/2017 | Johnson | |
| 2017/0237554 A1 | 8/2017 | Jacobs et al. | |
| 2017/0323294 A1 | 11/2017 | Rohlfing et al. | |
| 2017/0337534 A1* | 11/2017 | Goeringer | H04L 63/12 |
| 2017/0372308 A1 | 12/2017 | Metnick | |
| 2018/0204191 A1 | 7/2018 | Wilson | |
| 2019/0013933 A1* | 1/2019 | Mercuri | G06F 16/904 |
| 2019/0080392 A1* | 3/2019 | Youb | G06F 21/64 |
| 2020/0184489 A1 | 6/2020 | Negi | |

FOREIGN PATENT DOCUMENTS

| | | |
|---|---|---|
| CN | 102948128 | 2/2013 |
| CN | 106462547 | 2/2017 |
| EP | 3073670 | 9/2016 |

OTHER PUBLICATIONS

Application No. EP18852014.2, Extended European Search Report, dated Sep. 24, 2020, 9 pages.

Thomas et al., "The Interledger Protocol Draft-Thomas-Interledger-00", Available Online at: https://tools.ietf.org/pdf/draft-thomas-interledger-00.pdf, Jul. 8, 2016, 13 pages.

Wang et al., "Blockchain Router: A Cross-Chain Communication Protocol", Informatics, Environment, Energy and Applications, Mar. 29, 2017, pp. 94-97.

White et al., "Implementing VPNs in a z/OS Environment", Available Online at: https://www.redbooks.ibm.com/redbooks/pdfs/sg246530.pdf, Jan. 2002, 188 pages.

Application No. EP18852014.2, Office Action, dated Feb. 17, 2022, 4 pages.

Application No. CN201880054909.1, Office Action, dated Feb. 18, 2023, 19 pages.

\* cited by examiner

LAYERED RECORDING NETWORKS

CROSS REFERENCE TO RELATED APPLICATIONS

This application is a continuation application of U.S. application Ser. No. 16/630,838, filed Jan. 13, 2020, which is a 35 U.S.C. 371 patent application of international application number PCT/US2018/048173, which claims the benefit of the filing date of U.S. Patent Application No. 62/551,013, filed on Aug. 28, 2017, which is herein incorporated by reference in its entirety for all purposes.

BACKGROUND

Many networks and applications exist for recording information. For example, there are multiple systems and networks designed for recording patient medical information, such as various hospital-specific networks and insurance provider-specific networks. Similarly, there are multiple distinct networks for managing voter registration data (e.g., at various local, state, and national levels). Additional networks exist for recording information about transferring assets and data. For example, multiple distinct networks exist for transferring access credentials, event tickets, property rights, currency, game credits, mobile phone minutes, digital media, etc. In the case of event tickets, if someone wants to transfer an event ticket to a friend, they can choose one of several ticket transfer networks and applications.

It can be beneficial to unify and simplify many types of information recording networks. For example, if all networks for transferring mobile phone minutes were combined into a single, global network, it could simplify the transfer process. Participants could have just one application which is configured for the one network. Additionally, it could simplify record keeping, as one network could keep track of where all mobile phone minutes have been moved.

However, unifying recording networks can present new problems. For example, coordinating all new records and/or transfers can be a large task, and may be too large a burden for a single network coordinator. Additionally, the network coordinator may be able to view the details of every transfer. This can limit privacy for network participants, and may provide too much power to the network coordinator.

Embodiments of the invention address these and other problems individually and collectively.

SUMMARY

Embodiments of the invention provide systems and methods for making distinct networks interactive. In some embodiments, instead of providing a single global network, multiple independent networks can be established. These networks can be referred to as child networks. The child networks can each be configured to interact with a parent network. For example, a coordinator for a child network can also act as a participant in the parent network, and can thereby relay some information between the child network and parent network. If each child network interacts with the parent network, the different child networks can be indirectly connected to one another through the parent network. This allows a value transfer to take place between participants in different child networks. As a result, separate child networks can maintain privacy and customizable local rules and procedures, and at the same time a global-level of connectivity is established.

One embodiment of the invention is directed to a method. The method comprises receiving, by a network coordinator computer, from a node computer, a data package with first data. The network coordinator computer and the node computer are associated with a first network. The method also includes receiving a first digital signature associated with the first data. The first digital signature is generated with a first private key associated with the node computer. The method further comprises determining to transmit the data package to a second network, generating second data for the data package, and generating a second digital signature for the second data. The second digital signature is generated using a second private key associated with the network coordinator computer. The method also includes transmitting, to the second network, the data package including the first data, the second data, the first digital signature, and the second digital signature. The first network can be a child network, the second network can be a parent network, and the network coordinator computer can be a child network coordinator computer for a child network.

Another embodiment of the invention is directed to a network coordinator computer configured to perform the above-described method.

Another embodiment of the invention is directed to a method comprising receiving, by a second network coordinator computer associated with a second network, from a first network coordinator computer associated with a first network, a data package including first data and second data, a first digital signature, and a second digital signature. The first data was generated by a node computer, and the first digital signature was generated by the node computer using a first private key and the first data. The second data was generated by the first network coordinator computer, and the second digital signature was generated by the first network coordinator computer using a second private key and the second data. The method also includes generating third data for the data package, and generating a third digital signature for the third data. The third digital signature was generated using a third private key associated with the second network coordinator computer. The method further comprises transmitting, to a third network, the data package including the first data, the second data, the third data, the first digital signature, the second digital signature, and the third digital signature. The first network can be a first child network, the second network can be a parent network, the third network can be a second child network, and the network coordinator computer can be a parent network coordinator computer for the parent network.

Another embodiment of the invention is directed to a second network coordinator computer configured to perform the above-described method.

Further details regarding embodiments of the invention can be found in the Detailed Description and the Figures.

DETAILED DESCRIPTION

Figure 1:
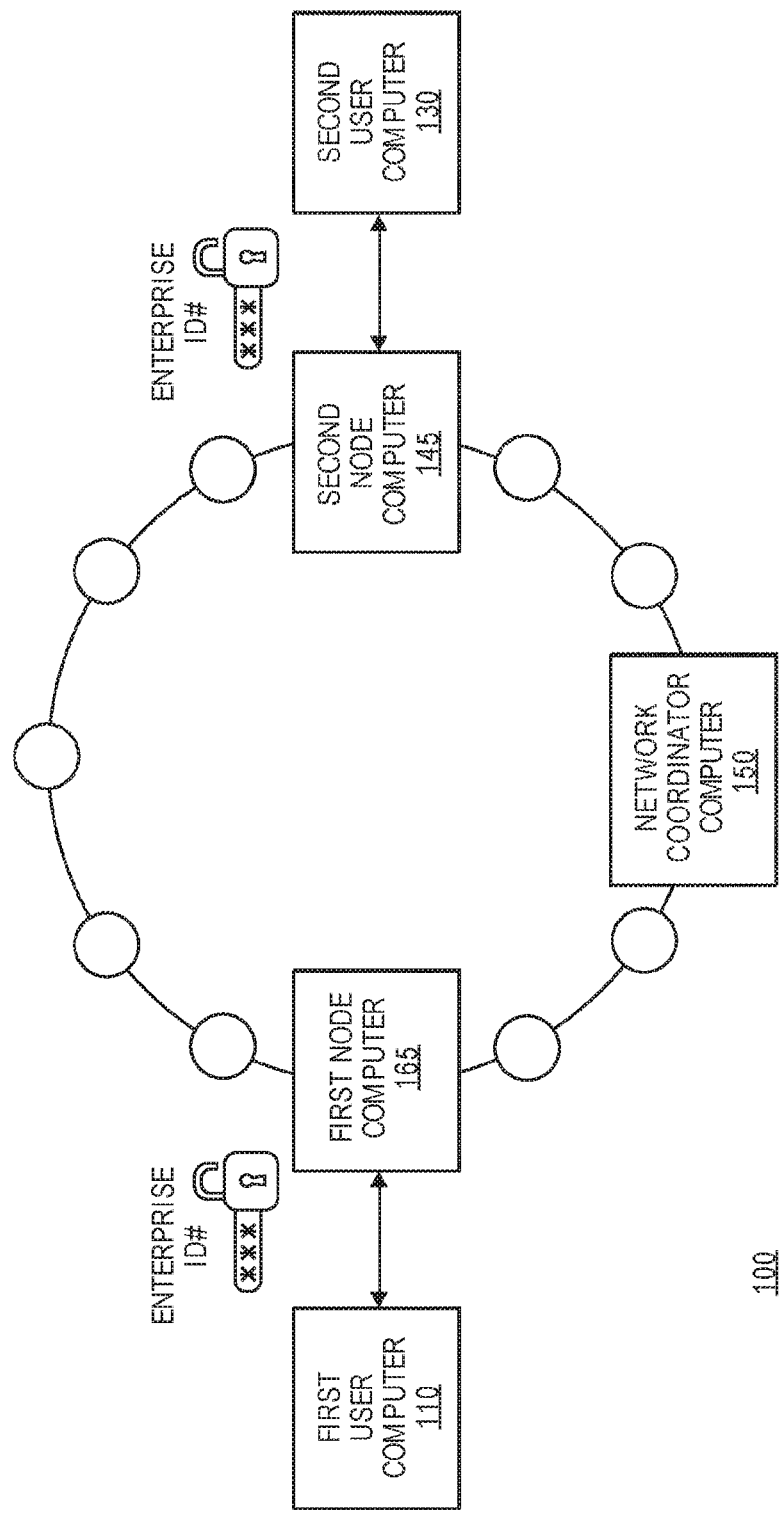
FIG. 1 shows a block diagram of a system with one network, according to an embodiment of the invention.

Embodiments of the invention provide systems and methods for layered and interactive recording networks. In some embodiments, multiple similar networks can be established. Each network can have a coordinator and multiple participants. The networks can have different participants and coordinators. The networks, referred to as child networks, can function independently, and can maintain their own distinct sets of records.

In some embodiments, the child networks can be connected, directly or indirectly, through a parent network. For example, each coordinator for each child network can also act as a participant (e.g., a node) in the parent network. As a result, each child network coordinator can communicate with the parent network. Through the parent network, the child networks can be indirectly connected. As a result, separate child networks can maintain privacy and customizable local rules and procedures, and at the same time a global-level of connectivity is established.

According to some embodiments, a value transfer or other record instruction can take place that involves multiple networks. For example, a first node in a first child network can create a data packet describing a payment instruction, where the payment is directed to another node in another child network. The coordinator of the first child network can receive the data packet and attempt to find the recipient node within the first child network. When the recipient is not found, the coordinator can then send the value transfer out of the child network in attempt to locate the recipient node in another network. For example, the coordinator computer can send the data package for the value transfer to the parent network (e.g., to a node in the parent network with which the coordinator is associated). A parent network coordinator can then identify another child network with which the recipient node is located, and then forward the data package to that child network. Once the data package arrives in the correct child network, it can finally be provided (e.g., by the coordinator of that network) to the recipient node. Thus, the connectivity of the child networks to the parent network allows a value transfer can take place across networks.

When a participant (e.g., a node computer) first initiates a value transfer, it may create a data package that details the sending node and a recipient node. However, if the value transfer is escalated to the parent network, the data package may be amended or modified. For example, the coordinator of the child network can add additional data, which may be referred to as second data, to the data package. The second data can specify that the recipient node was not found in the initial child network, and that the data package is being sent to another network. The second data may also indicate that the value transfer will now take place in multiple steps. For example, the second data can indicate that the value may first be transferred to an intermediary, such as the coordinator of the child network, before being transferred to the recipient node.

Additional modifications of this type can take place during the process of sending the data package to the recipient node, such as at other instances of the data package being sent into a new network. For example, coordinator of the parent network can further modify the data package if it determines that the data package is to be sent to a second child network. The parent network coordinator can generate third data and add the third data to the data package. The third data can specify that the recipient node was not found in the parent network, but that it is associated with a second child network, and that the data package is therefore being sent to the second child network. The third data may also indicate that the value transfer will now take place with additional steps. For example, the third data can indicate that the value may transferred through one or more additional intermediaries, such as the coordinator of the parent network and/or the coordinator of the second child network, before being transferred to the recipient node.

In some embodiments, a digital signature can be provided when a data package is modified. For example a coordinator can generate a digital signature based on the additional data and/or the original data package to indicate that the modification is authentic.

In further embodiments, a unique transaction identifier can be associated with a specific transaction and/or data package. The transaction identifier can serve to identify the transaction across some or all networks. For example, a parent network coordinator can generate unique transaction identifiers in a central location, and then distribute the transaction identifiers to different networks and coordinators. The child network coordinators can then assign transaction identifiers to transactions as they occur. When a data package or other transaction data is stored in a record, the transaction identifier can be stored as well. As a result, a given transaction can be identified across networks and records even after a data package has been modified. Additionally, separate network records (e.g., separate blockchains) can be partially linked through matching transaction identifiers.

Additional features that can be included in embodiments of the invention are described in the International Application US2017/046364, in the International Application US2017/059744, and in the International Application US2018/027455, each of which are incorporated by reference herein in their entirety for all purposes.

Prior to discussing specific embodiments of the invention, some terms may be described in detail.

An "interaction" may include an activity, exchange, or communication. Example interactions include performing a task (e.g., installing a pipe), a value transfer (e.g., a payment transaction or a transfer of access privileges), and providing updated information (e.g., medical records, academic records, etc.).

A "value" may include an amount, an asset, or a set of information with worth. For example, a value can include an amount of currency, access rights, or login credentials. A value can change ownership by being transferred from a first owner to a second owner. Examples of value transfers include payment transactions where currency is transferred, credit transfers such as where game credits or mobile phone minutes are transferred, and property transfers where event tickets or property deeds are transferred.

A "data package" may refer to a collection of digital information. For example, a data package can be information that exists in binary format. In some embodiments, a data package can include information about anything that can be described in a record, such as an interaction. For example, a data package can include any suitable type of digital information, such as transaction data, activity data, ownership data, product status data, project update data, etc. Embodiments allow a data package to include multiple sets of data. For example, a data package can include first data, second data, third data, and/or any other suitable portions of data. In some embodiments, a data package initially has first data, and then later second data is added in order to update or modify the data package.

A "network" may refer to a system of interconnected computers, peoples, organizations, or other entities. In some embodiments, a network can include a coordinating entity which can facilitate network operations. A network coordinating entity operate one or more network coordinating computers. Additionally, a network can include one or more network participants which may send and/or receive information within the network. An example of network participant can be a node.

The term "node" may refer to a connection point. In some embodiments, a node may be a physical electronic device that is capable of creating, receiving, or transmitting data. In other embodiments, a node may be a software module on a computing device, the software module a connection point in a communication network. In some embodiments, a node may be a computing device within a record-keeping network. A node may be able to create a data package, transfer a data package, receive a data package, validate a data package, access a central record, and/or perform any other suitable functions. Different types of nodes may be able to perform different sets of functions within a recording network. In some embodiments, a node may be associated with and/or operated by a financial institution computer (e.g., a bank), a payment processor computer, a third party computer, or any other suitable entity.

A "record" may refer to evidence of one or more interactions. A digital record can be electronic documentation of an interaction. A record can include a record identifier and record information. For example, record information can include information describing one or more interactions and/or information associated with the interactions (e.g., a digital signature). Record information can also include multiple data packets each of which include different data. A record identifier can be a number, title, or other data value used for identifying a record. A record identifier can be nondescript, in that it may not provide any meaningful information about the record information in the record. Examples of records include medical records, academic records, transaction records within a ledger of transactions, etc. Another example of a record is a block in a blockchain. An individual block can be an individual record, and a blockchain can be a series of records. A blockchain header is an example of a record identifier, and a blockchain body is an example of record information.

The term "ledger of transactions" may refer to a compilation of data from previous transactions. The ledger of transactions may be a database or other comparable file structure that may be configured to store data from all previous transactions, including the date and time of the transaction, the transaction amount, and identification information for the participants of the transaction (e.g., the sender and the receiver of the transaction amount). In some embodiments, the ledger of transactions may be in the form of an electronic ledger (e.g., blockchain) in which data already stored in the electronic ledger is unalterable.

A "blockchain" can be a database that maintains a continuously-growing list of records secured from tampering and revision. A blockchain may include a number of blocks of interaction records recorded on one or more nodes. Each block in the blockchain can contain also include a timestamp and a link to a previous block. For example, each block may include or be appended to a hash of the previous block. Stated differently, interaction records in a blockchain may be stored as a series of "blocks," or permanent files that include a record of a number of transactions occurring over a given period of time. Blocks may be appended to a blockchain by an appropriate node after it completes the block and the block is validated. In embodiments of the invention, a blockchain may be distributed, and a copy of the blockchain may be maintained at each node in a blockchain network. In other embodiments, only a network coordinator may maintain the blockchain, and copies may not be maintained at other nodes.

A "key pair" may include a pair of linked encryption keys. For example, a key pair can include a public key and a corresponding private key. In a key pair, a first key (e.g., a public key) may be used to encrypt a message, while a second key (e.g., a private key) may be used to decrypt the encrypted message. Additionally, a public key may be able to verify a digital signature created with the corresponding private key. The public key may be distributed throughout a network in order to allow for verification of messages signed using the corresponding private key. Public and private keys may be in any suitable format, including those based on RSA or elliptic curve cryptography (ECG). In some embodiments, a key pair may be generated using an asymmetric key pair algorithm. However, a key pair may also be generated using other means, as one of ordinary skill in the art would understand.

The term "digital signature" may refer to an electronic signature for a message. A digital signature may be a numeric data value, an alphanumeric data value, or any other type of data including a graphical representation. A digital signature may be a unique data value generated from a message (or data packet) and a private key using an encrypting algorithm. In some embodiments, a validation algorithm using a public key may be used to verify the signature.

An "enterprise identifier" may include an identifier for a user. For example, an enterprise identifier can be a globally unique identifier for an end user that submits new record information to a node in a record-keeping network, or for an end user that receives information about new record information (e.g., a value transfer) from a node. In some embodiments, an enterprise identifier can also indicate a specific node with which a user is associated. An enterprise identifier may include alphanumeric characters, special characters, and any other suitable symbol.

An "address identifier" may include an identifier for a participant. For example, an address identifier can represent a node or a service provider in a network. In some embodiments, a communication can be directed to a specific node by including the node's address identifier. An address identifier can include a string of characters, such as letters, numbers, etc. For example, an address identifier can be a string of 5, 10, 15, or any other suitable number of characters. In some embodiments, a public key associated with a participant can be used as the participant's address identifier.

A "class identifier" may include a data value that represents a specific type of record. Class identifiers can be used to identify any suitable class of recordable information. For example, a class identifier can be configured to identify medical information-type records, academic credential-type records, product identifier-type records, employee data-type records, activity-type records (e.g., construction activities, plumbing activities, etc.), value transfer records of various types (e.g., US dollar payments, British pound payments, Chinese yuan payments, digital rights data transfers, property deed transfers, event ticket transfers, game credit transfers, energy credit transfers, mobile phone minute transfers, etc.), or any other suitable type of record. Classes can be divided in any suitable manner. In some embodiments, a class identifier can also indicate that a specific participant is authorized to create and/or receive data packages for that type of record. A class identifier can include a string of characters, such as letters, numbers, etc. For example, an address identifier can be a string of 5, 10, 15, or any other suitable number of characters.

A "server computer" may include a powerful computer or cluster of computers. For example, the server computer can be a large mainframe, a minicomputer cluster, or a group of servers functioning as a unit. In one example, the server computer may be a database server coupled to a Web server. The server computer may be coupled to a database and may include any hardware, software, other logic, or combination of the preceding for servicing the requests from one or more client computers.

As mentioned above, embodiments of the invention enable multiple local networks to be created, each of which communicate with a central parent network. Before describing these interactive networks in detail, a single network will be described for explanatory purposes. The components and functionality of the single network can apply to each of the child networks and the parent network. The child networks can essentially be copies of the single network described below, according to some embodiments.

FIG. 1 shows a system 100 comprising a number of components. The system 100 comprises a single recording network that is administered by a network coordinator computer 150. The first node computer 165, the second node computer 145, and any other suitable number of node computers participate in the network. The first user computer 110 operated by a first user (not shown) can submit record update instructions via the first node computer 165, and the second user computer 130 operated by a second user (not shown) can receive record updates via the second node computer 145. All of the computers shown in the system 100 may be in operative communication with each other through any suitable communication channel or communications network. Suitable communications networks may be any one and/or the combination of the following: a direct interconnection; the Internet; a Local Area Network (LAN); a Metropolitan Area Network (MAN); an Operating Missions as Nodes on the Internet (OMNI); a secured custom connection; a Wide Area Network (WAN); a wireless network (e.g., employing protocols such as, but not limited to a Wireless Application Protocol (WAP), I-mode, and/or the like); and/or the like.

Messages between the computers, networks, and devices may be transmitted using a secure communications protocols such as, but not limited to, File Transfer Protocol (FTP); HyperText Transfer Protocol (HTTP); Secure Hypertext Transfer Protocol (HTTPS), Secure Socket Layer (SSL), ISO (e.g., ISO 8583) and/or the like.

The system 100 can be configured to create and maintain records of any suitable types. The network coordinator computer 150 can coordinate and administrate the record-keeping process by providing a number services. For example, the network coordinator computer 150 can build new blocks for a blockchain, the new blocks including updated record information. The network coordinator computer 150 can also enroll nodes and end users, as well as regulate the behavior of participating nodes in order to keep the records secure and reliable. The network coordinator computer 150 can further verify new data packages and inform participating nodes about new interactions and blocks.

While the network coordinator computer 150 can build and maintain the records, the first node computer 165 and the second node computer 145 can submit new information to the network coordinator computer 150 for recording. The first node computer 165 and the second node computer 145 can do this by creating and submitting data packages with interactions of various classes. The first node computer 165 and the second node computer 145 can create data packages based on interaction instructions received from the first user computer 110 and/or the second user computer 130.

While FIG. 1 specifically illustrates the first node computer 165 and the second node computer 145, the system 100 can include any suitable number of additional node computers (as represented by the empty circles in FIG. 1). Additionally, the first node computer 165 and second node computer 145 can communicate with other user computers beyond the first user computer 110 and the second user computer 130. Further, the system 100 can include more than one network coordinator computer 150 for administering the recording network.

The system 100 may be used to process, approve, and record any suitable type of information. For example, the system 100 can be used to record information about new interactions, such as new projects and activities, new value transfers, new medical patient data, new academic achievements, etc.

Figure 2:
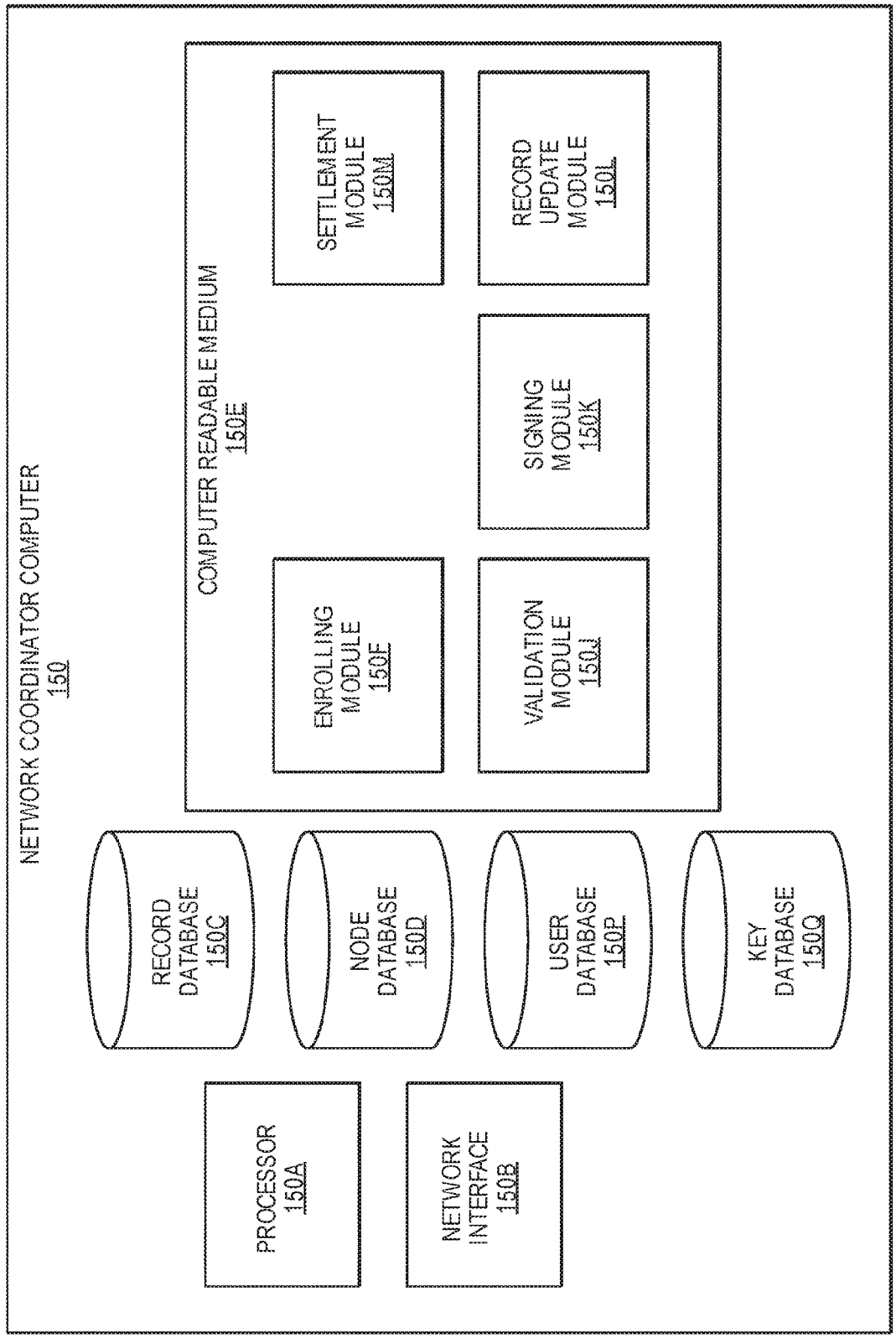
FIG. 2 shows a block diagram of a network coordinator computer, according to an embodiment of the invention.

An example of a network coordinator computer 150, according to some embodiments of the invention, is shown in FIG. 2. The network coordinator computer 150 comprises a processor 150A, a network interface 150B, a record database 150C, a node database 150D, a user database 150P, a key database 150Q, and a computer readable medium 150E.

The record database 150C can store records. For example, interaction data received from nodes in the network can be inserted into a record and stored in the record database 150C. In some embodiments, the records can take the form of a blockchain with block records, each block including one or more data packages representing one or more interactions.

The node database 150D can include information about nodes, such as the first node computer 165 and the second node computer 145. For example, the node database can include identifiers associated with the first node computer 165, such as an address identifier and one or more class identifiers. The node database 150D can also include information about restrictions, such as spending limits, associated with different nodes.

The user database 150P can include information about enrolled end users, such as the first user and the second user, as well as devices associated with the users (e.g., the first user computer 110 and the second user computer 130). This can include enterprise identifiers, as well as information about with which node the user is associated. For example, the second user computers enterprise identifier can be associated with the second node computer's address identifier as well as a specific class identifier.

The key database 150Q can store encryption keys. For example, the key database 150Q can include a public key for each node, as well as a private key associated with the network coordinator computer 150. In some embodiments the key database 150Q can take the form of a hardware security module (HSM).

The computer readable medium 150E may comprise an enrolling module 150F, validation module 150J, a signing module 150K, a record update module 150L, a settlement module 150M, and any other suitable software module.

The enrolling module 150F may comprise code that causes the processor 150A to enroll node computers for joining the recording network. For example, the enrolling module 150F may contain logic that causes the processor 150A to evaluate whether or not an entity can enroll, as well as what level of risk to assign to a new entity. A risk level can be affected by whether the entity is a well-known and reliable organization, whether it has established a settlement account or other settlement processes, whether it is located in a risky country, etc. In addition to assigning a risk level, the network coordinator computer 150 can issue activity limits for the node based on the risk profile. Activity limits can include, for example, maximum transaction threshold limits and/or velocity limits, such as a limit on the number of payment transactions or total transaction value that can be submitted within a certain time period (e.g., a day, a week, or a month).

The enrolling module 150F may also include instructions for generating and assigning a unique address identifier for a newly enrolled node. Additionally, there may be instructions for generating and distributing keys to a newly enrolled node. For example, the network coordinator computer 150 may generate a key pair for a node. The network coordinator computer 150 can store the public key and provide the private key to the node computer.

The enrolling module 150F can further include instructions for enrolling end users. For example, the network coordinator computer 150 can receive information about a new user (e.g., a name, address, account number, phone number, a business' corporate profile, etc.) from a node, store the user information, and then assign a unique enterprise identifier to the user. In some embodiments, the enterprise identifier can include a subset of characters that are indicative of the associated node or the node's address identifier.

The validation module 150J may comprise code that causes the processor 150A to validate a new data package so that the data package can be entered in the records. For example, the validation module 150J may contain logic that causes the processor 150A to check that a data package includes an address identifier and a class identifier are both valid and associated with the same node computer, and to check that limits associated with the submitted class identifier have not been exceeded and are not currently being exceeded by the new data package.

The validation module 150J may further contain logic that causes the processor 150A to verify that all entities associated with the data package (e.g., one or more nodes, and one or more users) are registered with the network and have been screened for compliance. The network coordinator computer 150 can also evaluate transaction risk, for example by assessing the transaction velocity of one or more parties involved, or by determining whether the submitting node has any warnings issued.

The validation module 150J may further comprise code that causes the processor 150A to verify the authenticity of one or more digital signatures. For example, the validation module 150J may contain logic that causes the processor 150A to use a node computers public key to verify the authenticity of a digital signature associated with that node computer.

The signing module 150K may comprise code that causes the processor 150A to generate digital signatures. For example, the signing module 150K may contain logic that causes the processor 150A to generate a digital signature for a data package using a network coordinator private key. The network coordinator computer's digital signature can serve to indicate the authenticity of a data package, and can provide a guarantee that a transfer is valid and trustworthy.

In some embodiments, a digital signature can activate a smart contract. For example, a first smart contract may hold the first node computer 165 liable for the transaction, and a second smart contract may further hold the network coordinator computer 150 liable for the transaction in case the first node computer 165 cannot complete the transaction. Smart contracts can automatically initiate a settlement process after a certain amount of time. In some embodiments, the network coordinator computer 150 can force settlement between two accounts at a central bank.

The record update module 150L may comprise code that causes the processor 150A to maintain and update a set of records. For example, the record update module 150L may contain logic that causes the processor 150A to record information about a new interaction (e.g., as indicated in a new data package). In some embodiments, the record update module 150L may include instructions for including a new data package in the next blockchain block.

The record update module 150L may further include instructions for, when a new data package is created, informing the parties associated with the interactions described in the data package. For example, when a new payment transaction is validated and signed, the network coordinator computer 150 may send information about the new payment transaction to a receiving node (e.g., the second node computer 145) and/or the user computers.

In some embodiments, the participating node computers may not maintain a separate set of records, and may instead refer to the centrally-maintained records of the network coordinator computer 150. For example, the first node computer 165 and the second node computer 145 may each be light nodes. In such a case, the network coordinator computer 150 may provide these nodes with real-time access to the central records, or the network coordinator computer 150 may provide regular record updates (e.g., updates can be sent every 10 seconds, 1 minute, 5 minutes, etc.). As a result, other nodes may be aware of new interactions immediately or soon after the interactions are recorded.

In some embodiments, participating node computers may not be able to see all of the record information, and they may instead have a filtered or permissioned view of the records. For example, the first node computer 165, the second node computer 145, the first user computer 110, and/or the second user computer 130 may only be able to view interaction records with which they are associated (e.g., transactions to which they are a party) when accessing the records at the network coordinator computer 150. For example, the second node computer 145 may be able to view all block headers, but may only be able to view block bodies and interaction records with which it is associated.

In some embodiments, there may be multiple network coordinator computers 150 within one network that each receive and process different data packages with information about different interactions, and then update their own records. These different network coordinator computers may communicate with one another to share new records and to confirm that their records include the same interactions.

The settlement module 150M may comprise code that causes the processor 150A to settle a promised value between accounts. For example, the settlement module 150M may contain logic that causes the processor 150A to debit the first node's settlement account at a central bank by an amount indicated in an interaction record, and to credit the second node's settlement account with that same amount (or that amount less assessed fees).

Referring back to FIG. 1, the first node computer 165 can, as mentioned above, participate in the recording network by creating and submitting new data packages with new interaction data in order to update the records on behalf of one or more users.

Figure 3:
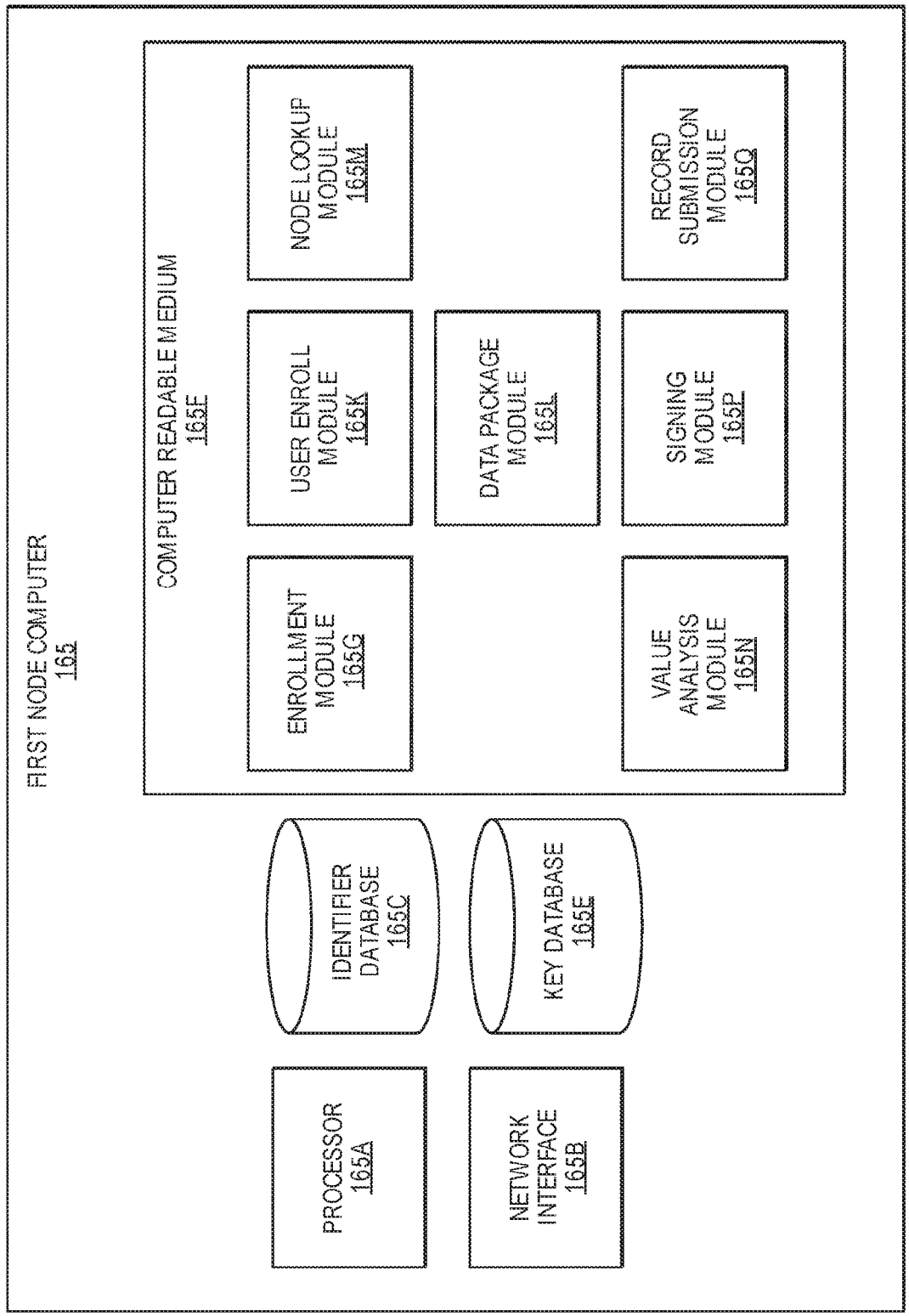
FIG. 3 shows a block diagram of a first node computer, according to an embodiment of the invention.

An example of a first node computer 165, according to some embodiments of the invention, is shown in FIG. 3. The first node computer 165 comprises a processor 165A, a network interface 165B, an identifier database 165C, a key database 165E, and a computer readable medium 165F.

The identifier database 165C can store information about the first node computer's identifiers, such as an address identifier and one or more class identifiers. The identifier database 165C may also include information about one or more users, such as an enterprise identifiers, an associated class type, and/or a user account.

The key database 165E can store encryption keys. For example, the key database 165E can include a private key associated with the first node computer 165, as well as a public key associated with the network coordinator computer 150. In some embodiments the key database 165E can take the form of a hardware security module (HSM).

The computer readable medium 165F may comprise an enrollment module 165G, a user enroll module 165K, a data package module 165L, a node lookup module 165M, a value analysis module 165N, a signing module 165P, a record submission module 165Q, and any other suitable software module.

The enrollment module 165G may comprise code that causes the processor 165A to enroll with the network coordinator computer 150 for participation in the recording network. For example, the enrollment module 165G may contain logic that causes the processor 165A to send an enrollment request message including information about the first node, such as an address, a bank identifier, a settlement account, and/or any other suitable information. The enrollment module 165G also include instructions for receiving and storing an address identifier, a network coordinator public key, a first node private key, one or more class identifiers, and any other suitable enrollment information from the network coordinator computer 150.

The user enroll module 165K may comprise code that causes the processor 165A to facilitate enrollment of end users. For example, the user enroll module 165K may contain logic that causes the processor 165A to provide user information (e.g., a name, a residential and/or business address, a date of birth, a phone number, an account number, an account username, an account password, an email address, a government-issued identification number such as a driver's license number, passport number, or social security number, etc.) to the network coordinator computer 150. The first node computer 165 can also receive and store an enterprise identifier for the first user computer 110 from the network coordinator computer 150, and provide the enterprise identifier to the first user computer 110.

The data package module 165L may comprise code that causes the processor 165A to generate a new data package. For example, the data package module 165L may contain logic that causes the processor 165A to receive an instruction from the first user computer 110, and to create a data package for one or more interactions based on the instruction. The data package can include any suitable information for entering a new record into a ledger. In the example of payment transactions, the data package can include information about the sending account, the receiving account, the sending currency, the receiving currency, and/or any other suitable information.

The node lookup module 165M may comprise code that causes the processor 165A to identify a node based on a user. For example, the node lookup module 165M may contain logic that causes the processor 165A to identify the second node computer based on the second user computer being indicated as a transaction recipient. For example, the second node's address identifier may be identified based on a subset of characters included in the second user's enterprise identifier, or the address identifier can be associated with the second user's enterprise identifier in a database (e.g., a database accessed at the network coordinator computer 150). The node lookup module 165M can also include instructions for adding an identified address identifier to a new data package.

The value analysis module 165N may comprise code that causes the processor 165A to determine a value for an interaction. For example, the value analysis module 165N may contain logic that causes the processor 165A to determine a first amount in a first currency that will be charged to the first user computer 110 in order to deliver a second amount in a second currency to the second user computer 130. This determination can include looking up a current foreign exchange rate and calculating transfer fees (e.g., both of which can be provided by the network coordinator computer 150). The amount debited in the first currency, the amount credited in the second currency, the currency exchange rate, and/or the fees assessed can be included in a new data package.

The signing module 165P may comprise code that causes the processor 165A to create a digital signature. For example, the signing module 165P may contain logic that causes the processor 165A to apply a private key and a mathematical algorithm to a data package, such that the digital signature is generated for the data package. The first node computer's digital signature can serve as evidence that it truly was the first node computer 165 that created and submitted the data package.

The record submission module 165Q may comprise code that causes the processor 165A to submit a new data package with new interactions for recording. For example, the record submission module 165Q may contain logic that causes the processor 165A to send a new data package, an associated digital signature, and/or any other suitable information to the network coordinator computer 150.

In some embodiments, the first node computer 165 can provide additional services to a user beyond submitting new data packages with new interactions to the recording network. For example, the first node computer 165 can be a computer associated with a financial institution, a hospital, a government agency, an academic institution, a mobile phone service provider, or any other suitable service provider. Accordingly, in some embodiments, the first node computer 165 can maintain an account on behalf of the user. The account may store identity information, medical records, academic records, financial information, or any other suitable details depending on the type of service provider.

In embodiments where the first node computer 165 is associated with a financial institution, the first node computer 165 may store value on behalf of the user. The first node computer 165 may also be able to provide value (e.g., provide a payment) on behalf of the user. An example of a financial institution is an issuer, which may typically refer to a business entity (e.g., a bank) that issues and maintains an account (e.g., a bank account) for a user.

In some embodiments, the first node computer 165 can be representative of multiple associated computers. For example, the functionality described above for network participation and the functionality associated with banking services can be divided among several cooperative computers.

Referring back to FIG. 1, the second node computer 145 can, as mentioned above, participate in the recording network. In some embodiments, the second node computer 145 can validate the authenticity of a new data package, and can inform the second user computer 130 about the new interaction data in the data package. The second node computer 145 can validate that a new data package is authentic in one or more manners. For example, the second node computer 145 can verify that the first node computer's digital signature and the network coordinator computers signature are both authentic (e.g., using their respective public keys). In some embodiments, the second node computer 145 can verify the authenticity of an interaction and/or data package by accessing a central record (e.g., a blockchain record), and confirming that the interaction and/or data package has been added to the records.

The second node computer 145 is primarily described herein as a node that receives information about a new interaction (e.g., via a data package) on behalf of the second user computer 130. However, in some embodiments, the second node computer 145 can include some or all of the functionality described above with respect to the first node computer 165. For example, the second node computer 145 can submit data packages with new interaction data to the recording network on behalf of the second user computer 130 or other associated users. Similarly, in some embodiments, the first node computer 165 can include some or all of the functionality described with respect to the second node computer 145 (e.g., the first node computer 165 can receive and validate data packages on behalf of the first user computer 110).

Similar to the first node computer 165, the second node computer 145 can also be associated with a service provider such as a bank. As a result, the second node computer 145 can host a second user account, and can store and receive a value on behalf of the second user. As an example the second node computer 145 can be associated with an acquirer, which may typically be a business entity (e.g., a commercial bank) that has a business relationship with a particular resource provider or other entity. Some entities can perform both issuer and acquirer functions. Some embodiments may encompass such single entity issuer-acquirers.

In some embodiments, second node computer 145 may have a high-level of trust that a promised value will be delivered, for example because of two valid digital signatures, because the interaction data is included in a blockchain record, because the data package includes several associated identifiers (e.g., a class identifier and/or an address identifier), and/or because of any other suitable evidence. As a result, the second node computer 145 may make a value indicated in a received data package immediately usable (e.g., withdrawable) in the second user's account, even if the value has not yet been settled and received. Additionally, the second node may have a high-level of trust in the network coordinator, as the network coordinator may be a large, trusted central entity.

As explained above, multiple nodes can join the recording network, and each node can send and receive data packages with interaction data on behalf of multiple users. A user can be an individual, a business, an organization's record-updating administrator, or any other suitable type of user. For example the first user can be an individual, and the second user can be a resource provider (e.g., a merchant) that engages in transactions and can sell goods or services, or provide access to goods or services.

In some embodiments, an end user can be associated with multiple enterprise identifiers. For example, a different enterprise identifier may be assigned to a user for each different currency and bank with which the user is associated. The first user can have multiple accounts at the first node computer 165, each with a different currency. Accordingly, the first user computer 110 can store a different enterprise identifier for each type of currency used with the first node computer 165. The first user may also engage in transactions using another account at a separate bank node, and may have another enterprise identifier associated with this additional bank.

Figure 4:
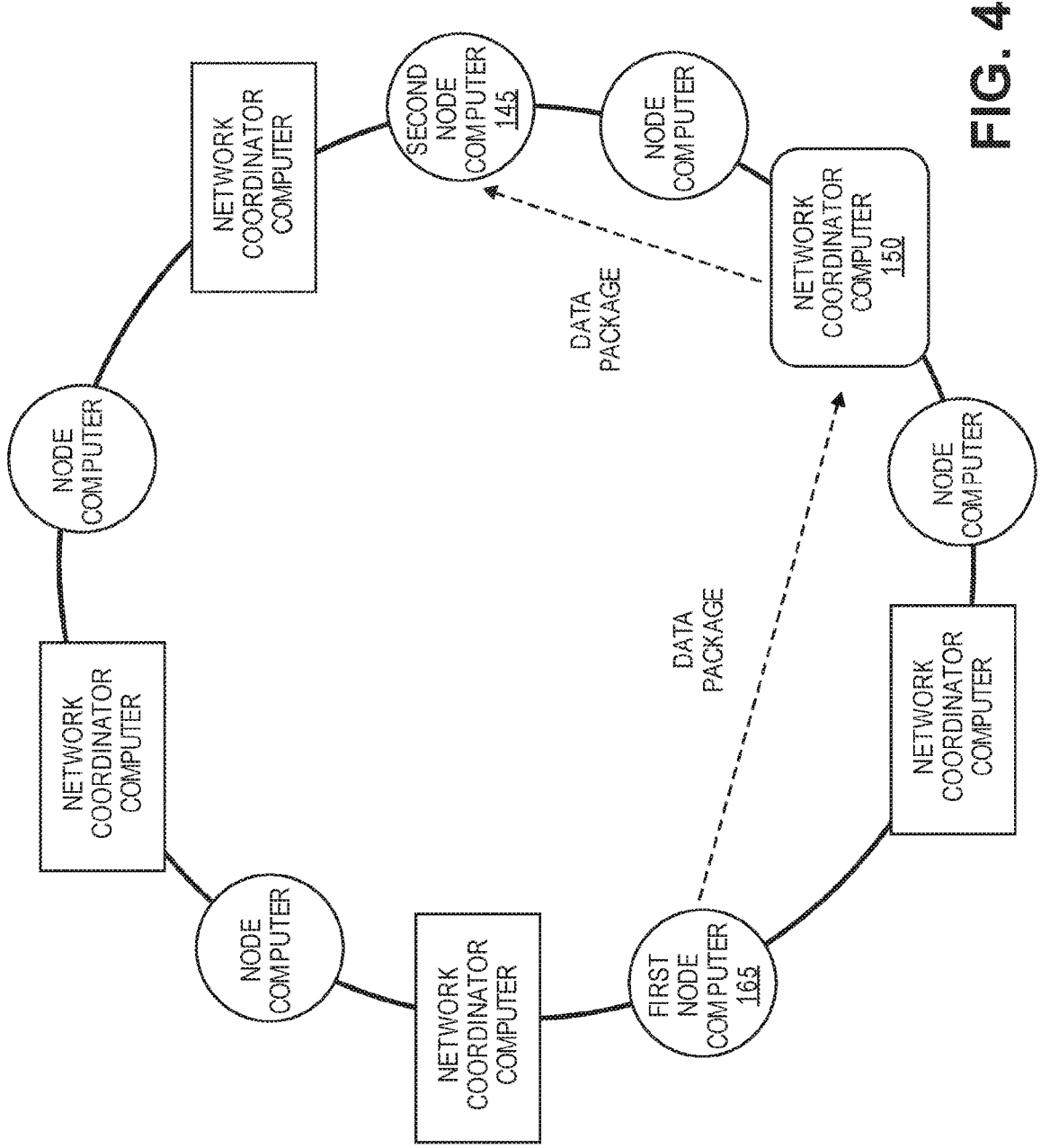
FIG. 4 shows an example of nodes in a network, according to an embodiment of the invention.

An example of a recording network is shown in FIG. 4. In some embodiments, as shown in FIG. 4, several nodes may be able to provide and receive data packages with interaction data within the recording network. An example transfer is shown, where an first node computer 165 is providing a data package with interaction data (e.g., for a payment transaction) to a second node computer 145. As shown, the first node computer 165 can send the data package to a network coordinator computer 150, which can then forward the data package to the second node computer 145. The network coordinator computer 150 can also validate and digitally sign the data package before sending to the second node computer 145. The recording network can include any other suitable number of node computers (e.g., which can act as senders and receivers), as well as additional network coordinator computers. Each network coordinator computer may maintain a ledger of interactions from data packages that have been transferred between the nodes, and the network coordinator computers can update one another to maintain synchronized ledgers.

As mentioned above, in some embodiments, the recording system may utilize a blockchain. Each block in the blockchain may include information about one or more interactions (e.g., from one or more data packages). A blockchain ledger may be unalterable without detection. This ensures that any tampering of information related to transactions, such as an attempt to reassign a transaction value to an inappropriate entity, will not go unnoticed. Together, a block header and a block body that includes the transaction information (e.g., and any other suitable information) can make up a block.

Figure 5:
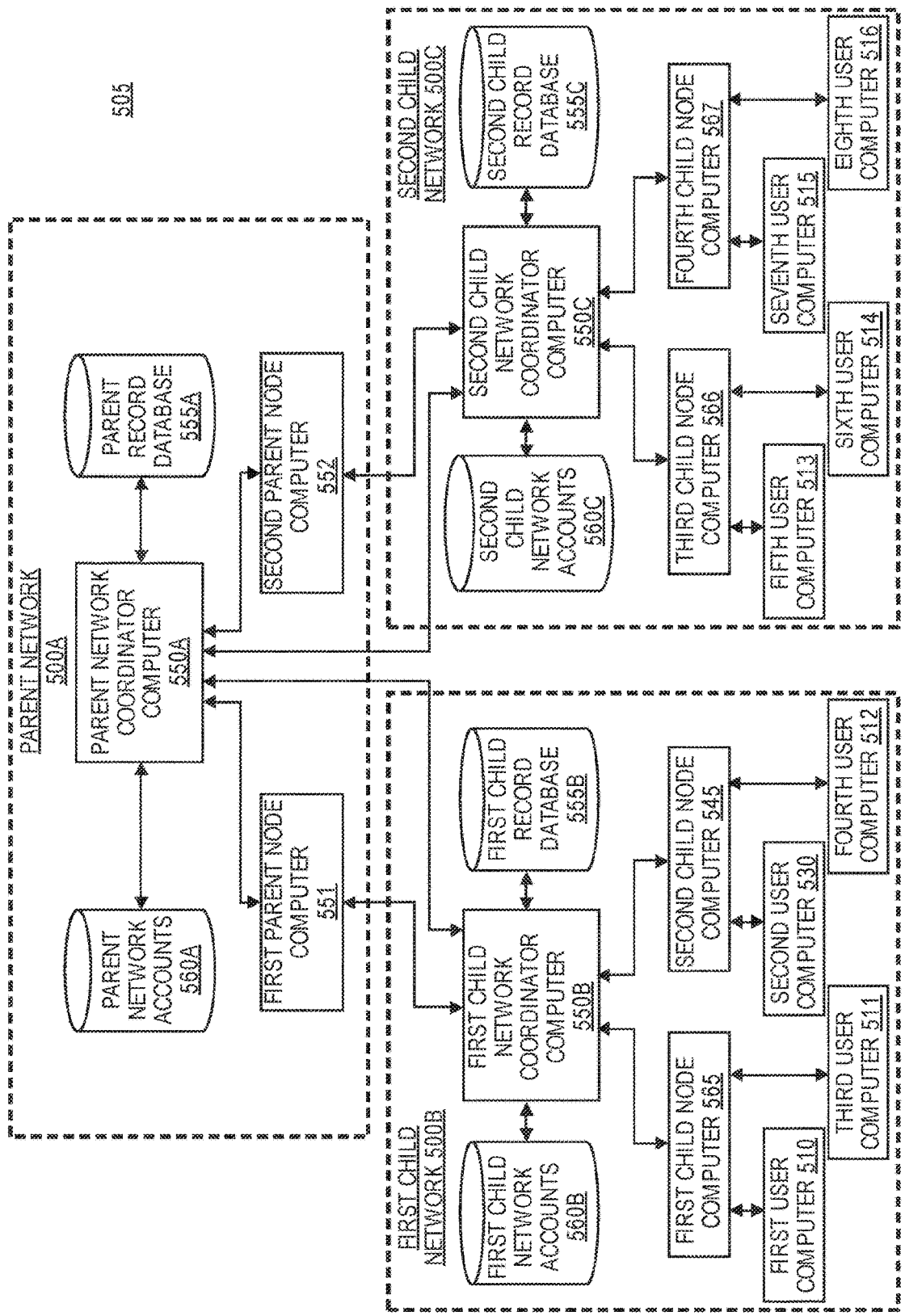
FIG. 5 shows a block diagram of a system with multiple networks, according to an embodiment of the invention.
Figure 6A:
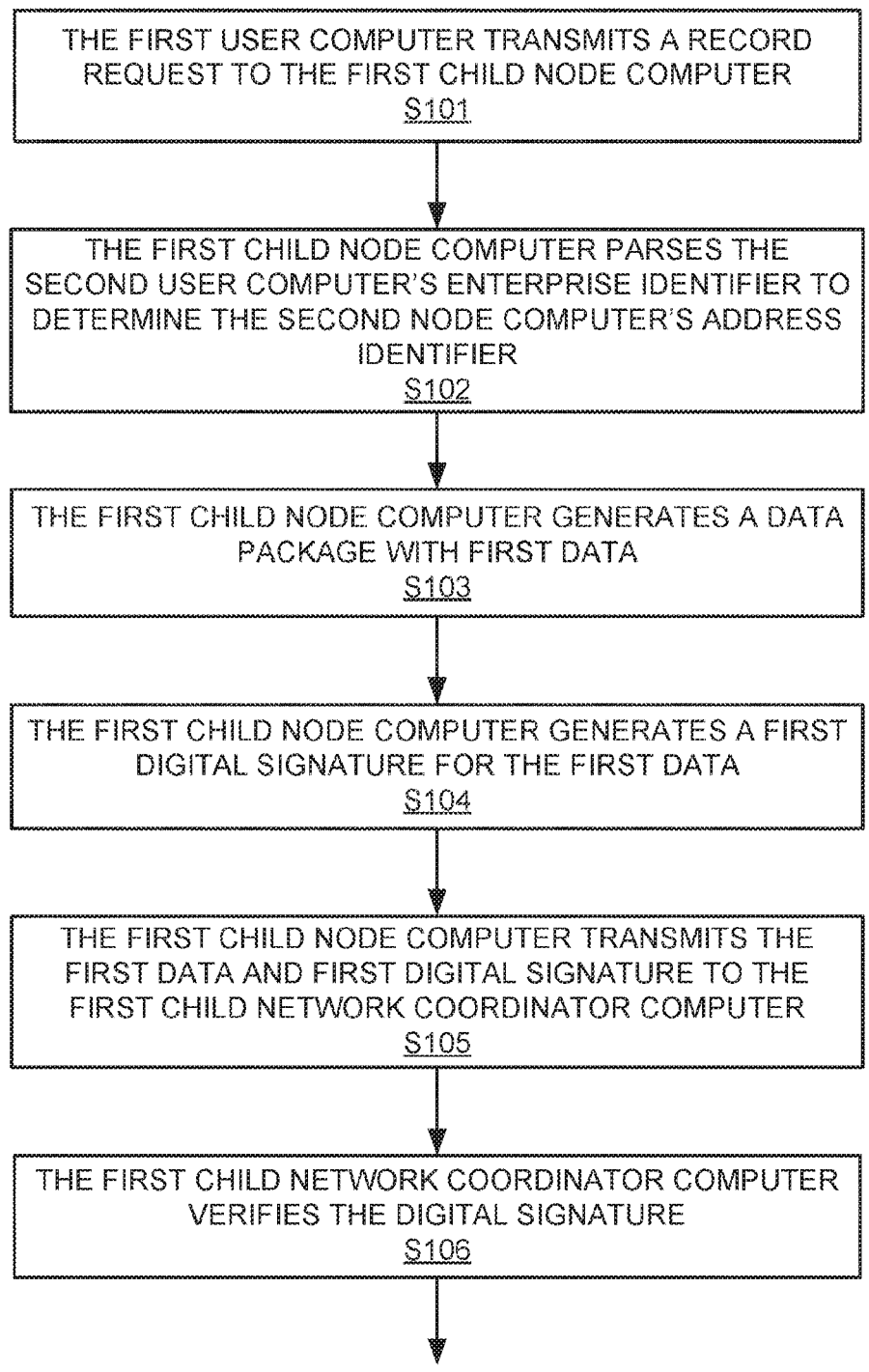
FIGS. 6A-6E shows a flow diagram illustrating a method, according to embodiments of the invention.
Figure 6B:
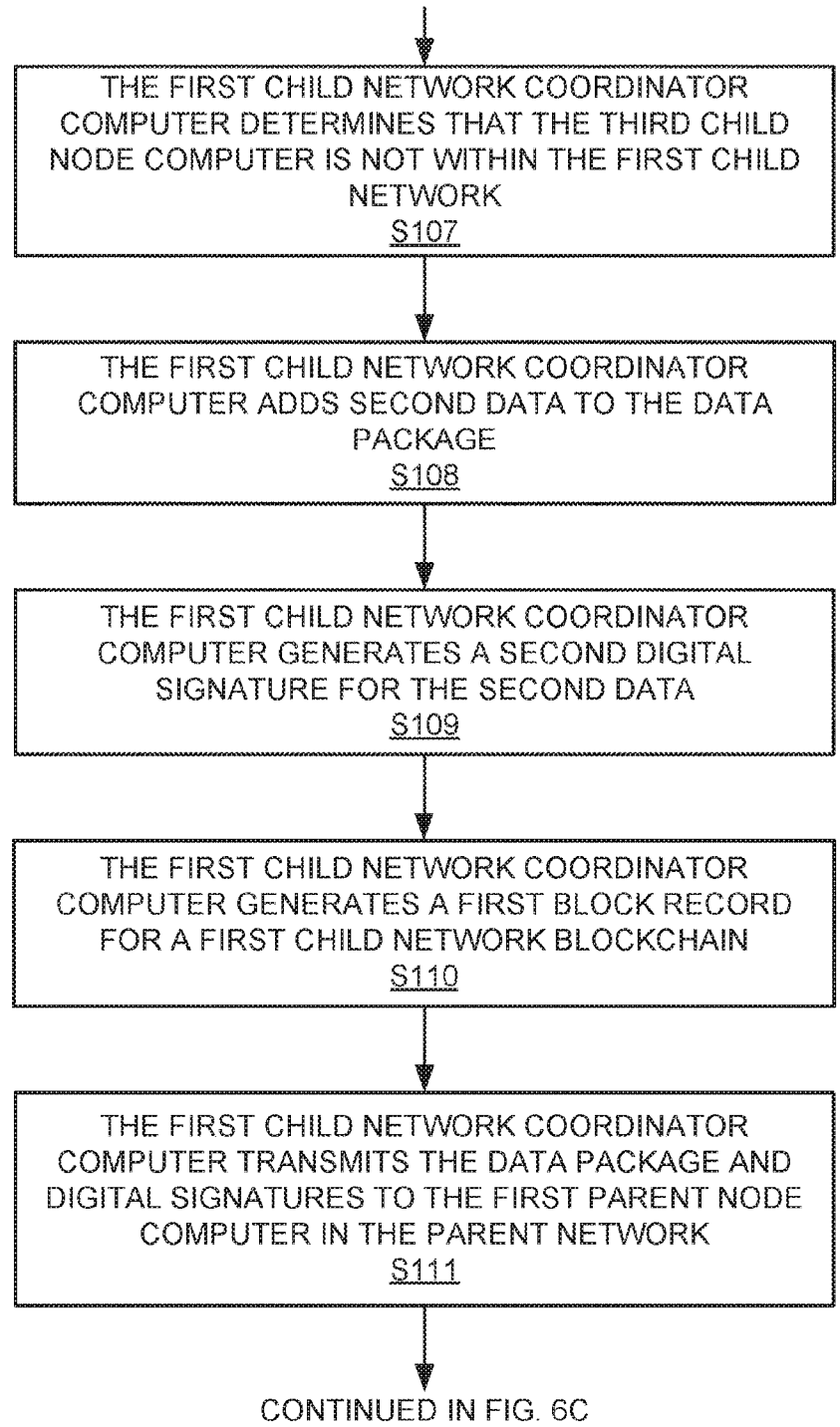
Figure 6C:
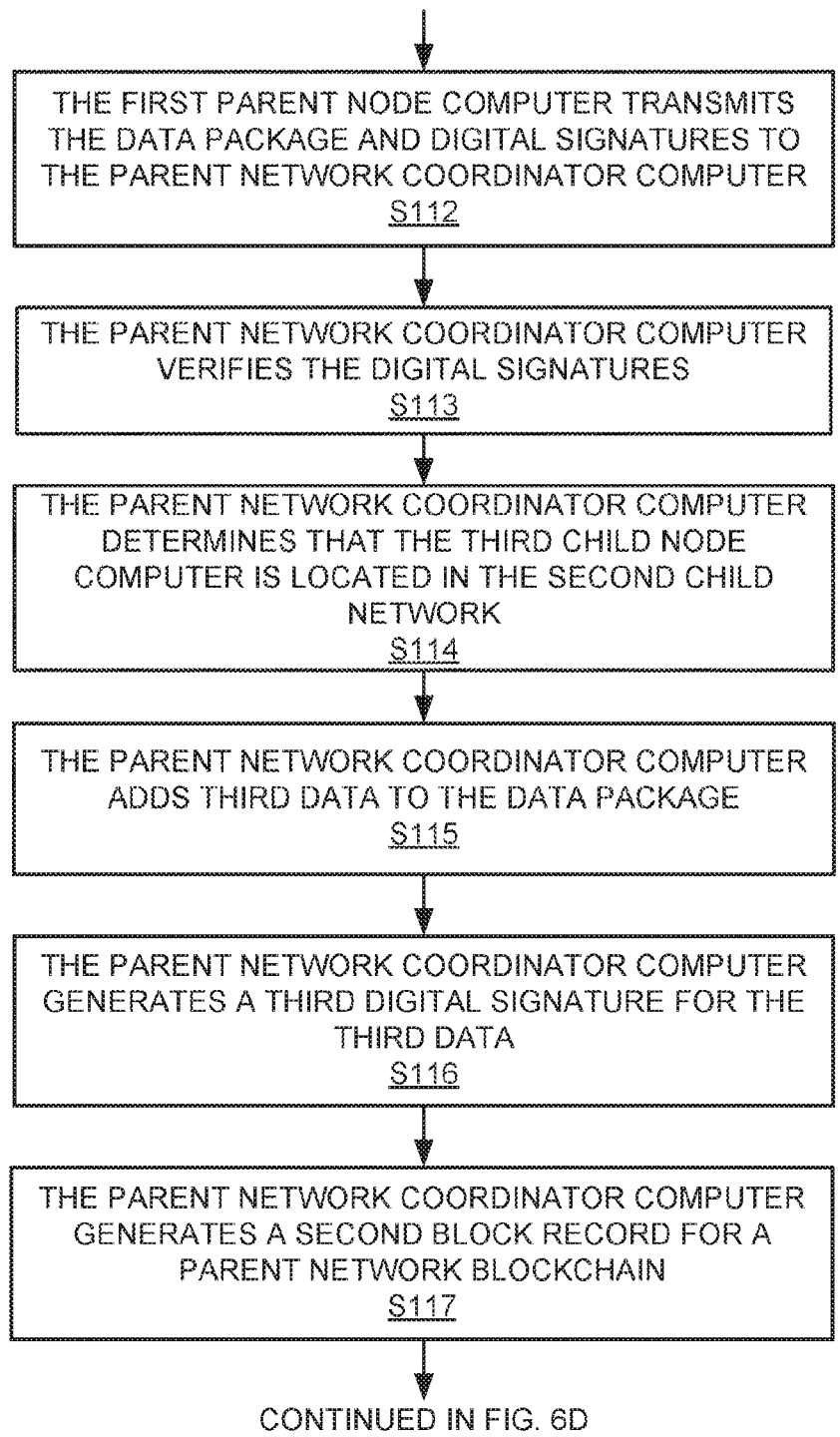
Figure 6D:
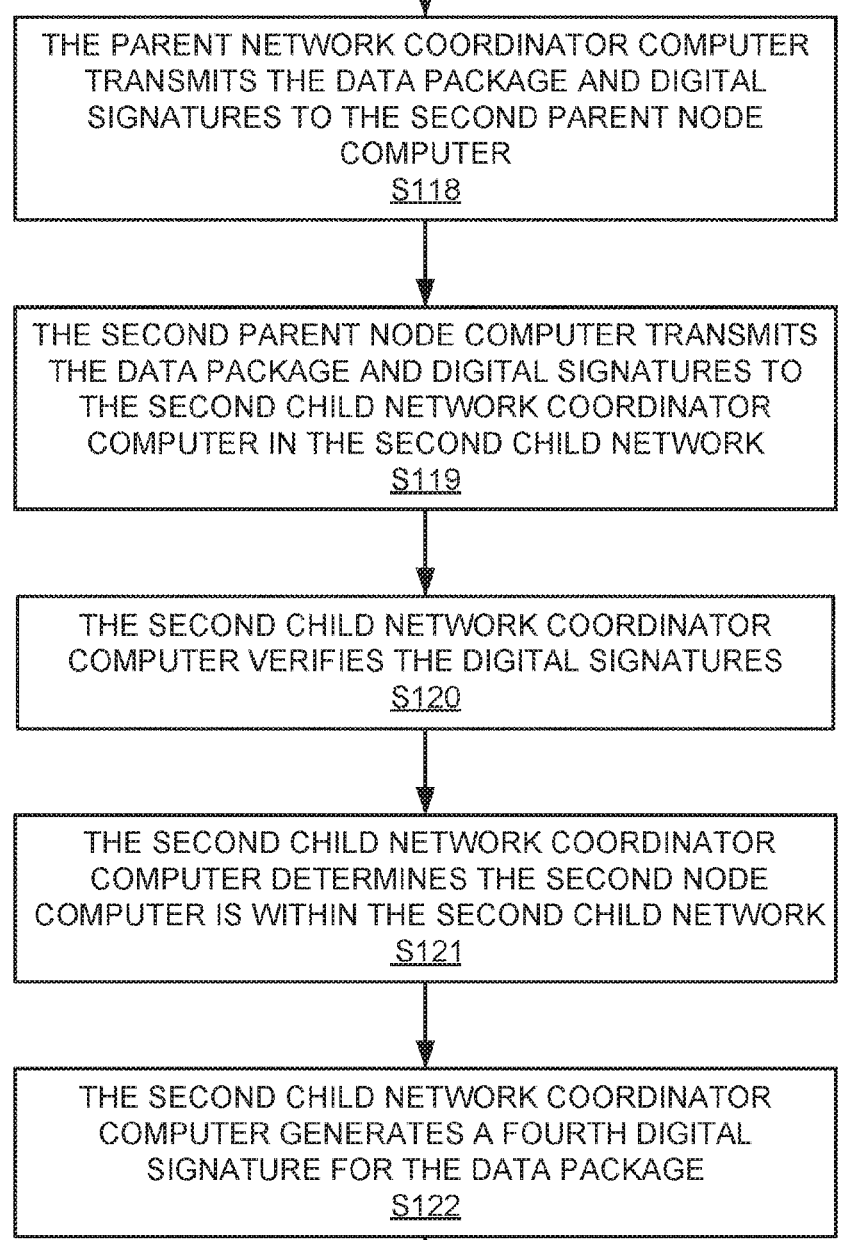
Figure 6E:
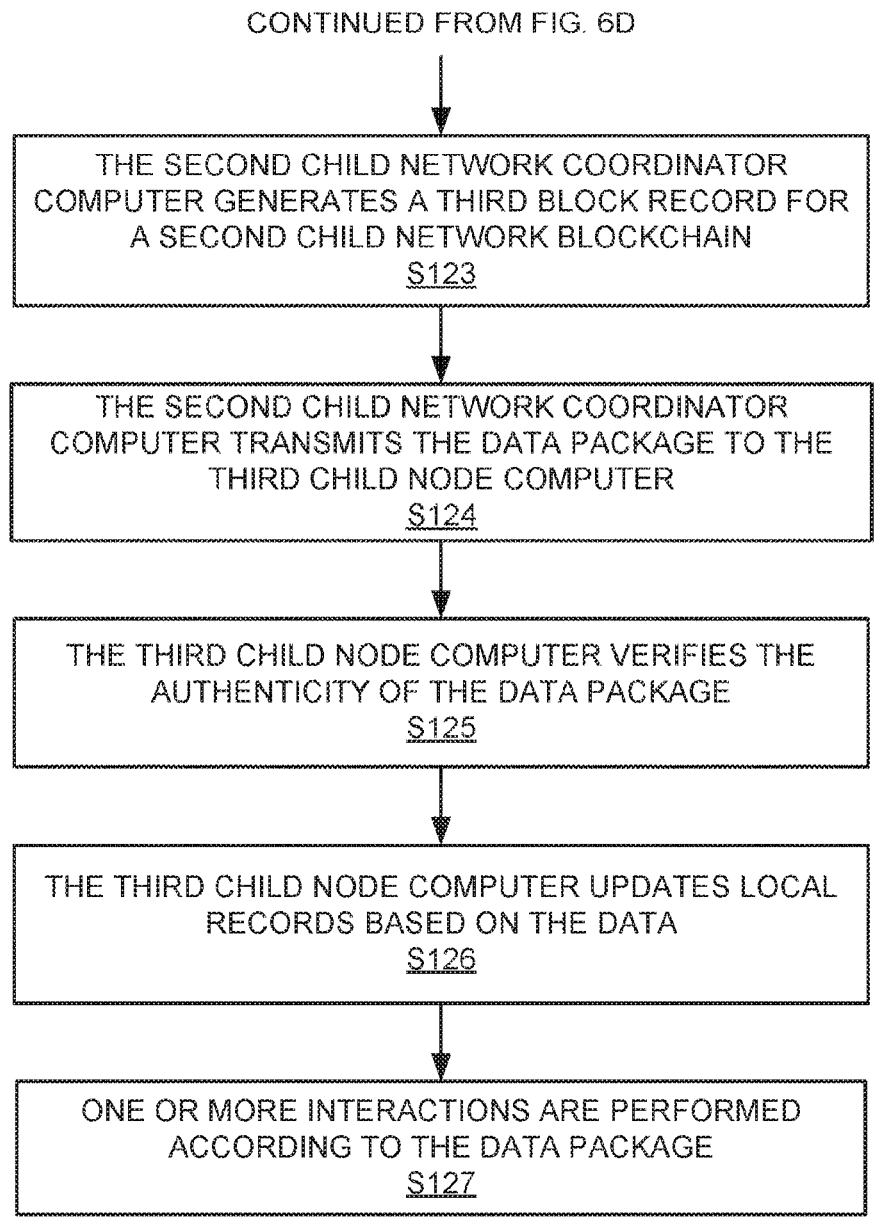

As mentioned above, in some embodiments, the recording network shown in FIG. 1 can be one of multiple recording networks. For example, FIG. 5 shows a system 505 with three separate, layered networks. The system 505 includes a parent network 500A, a first child network 500B, and a second child network 500C. Embodiments allow the system 505 to include additional child networks beyond what is shown in FIG. 5.

In some embodiments, the first child network 500B can be similar to or the same as the recording network shown in FIG. 1. For example, the first child network coordinator computer 550B in FIG. 5 can be the same as or similar to the network coordinator computer 150 in FIG. 1, the first child node computer 565 in FIG. 5 can be the same as or similar to the first node computer 165 in FIG. 1, the second child node computer 545 in FIG. 5 can be the same as or similar to the second node computer 145 in FIG. 1, the first user computer 510 in FIG. 5 can be the same as or similar to the first user computer 110 in FIG. 1, and/or the second user computer 530 in FIG. 5 can be the same as or similar to the second user computer 130 in FIG. 1. The first child record database 555B can be similar to or the same as the record database 150C shown in FIG. 2, and can store records for interactions within or involving the first child network 500B. The first child network accounts 560B can include accounts associated with each node and/or user within the first child network 500B for settling transactions.

Additionally, in some embodiments, the second child network 500C can be similar to or the same as the recording network shown in FIG. 1. For example, the second child network coordinator computer 550C in FIG. 5 can be the same as or similar to the network coordinator computer 150 in FIG. 1, the third child node computer 566 in FIG. 5 can be the same as or similar to the first node computer 165 in FIG. 1, the fourth child node computer 567 in FIG. 5 can be the same as or similar to the second node computer 145 in FIG. 1, the fifth user computer 513 in FIG. 5 can be the same as or similar to the first user computer 110 in FIG. 1, and/or the seventh user computer 515 in FIG. 5 can be the same as or similar to the second user computer 130 in FIG. 1. The second child record database 555C can be similar to or the same as the record database 150C shown in FIG. 2, and can store records for interactions within or involving the second child network 500C. The second child network accounts 560C can include accounts associated with each node and/or user in the second child network 500C for settling transactions.

Further, in some embodiments, the parent network 500A can be similar to or the same as the recording network shown in FIG. 1. For example, the parent network coordinator computer 550A in FIG. 5 can be the same as or similar to the network coordinator computer 150 in FIG. 1, the first parent node computer 551 in FIG. 5 can be the same as or similar to the first node computer 165 in FIG. 1, and/or the second parent node computer 552 in FIG. 5 can be the same as or similar to the second node computer 145 in FIG. 1. The parent record database 555A can be similar to or the same as the record database 150C shown in FIG. 2, and can store records for interactions within the parent network 500A. The parent network accounts 560A can include accounts associated with each node and/or user in the parent network 500A for settling transactions.

Accordingly, one or more of the parent network 500A, the first child network 500B, and the second child network 500C can be an independently operating recording network. Embodiments allow each network to have customized rules and procedures, and each network can include an exclusive set of type of participants. For example, the first child network 500B can be coordinated by a major financial institution, and the participants (e.g., nodes) can include smaller banks that have special relationships with the major financial institution. The second child network 500C can be similarly coordinated by a different major financial institution. The parent network 500A can be coordinated by a global, central coordinator such as a transaction processing network coordinator. Thus, embodiments allow separate recording networks to be created and customized for different groups and areas.

While the various networks can be effectively separate, they can become functionally interactive through entities that participate in two or more networks simultaneously. For example, in some embodiments, the operator of the first child network coordinator computer 550B in the first child network 500B can also operate the first parent node computer 551 in the parent network 500A. As a result, the coordinator of the first child network 500B can also be a participant in the parent network 500A. Embodiments allow the first child network coordinator computer 550B and the first parent node computer 551 to be a single computer, different parts of the same system, or otherwise associated with the same entity (e.g., a financial institution).

Accordingly, the first child network coordinator computer 550B can effectively communicate externally with other networks, via the first parent node computer 551. For example, if a transaction cannot be completed within the first child network 500B, the first child network coordinator computer 550B can escalate the transaction by sending a transaction data package to the first parent node computer 551. Within the parent network 500A, the first parent node computer 551 could send the data package to another node, such as the second parent node computer 552.

Embodiments allow other coordinators of other child networks to similarly participate in the parent network 500A, such that the parent network 500A can effectively connect some or all child networks. For example, the operator of the second child network coordinator computer 550C in the second child network 500C can also operate the second parent node computer 552 in the parent network 500A. As a result, a transaction data package received by the second parent node computer 552 in the parent network 500A can be forwarded to the second child network coordinator computer 550C in the second child network 500C, and then transmitted to any suitable node in the second child network 500C. Thereby, a transaction can take place between nodes in different child networks.

In some embodiments, networks can handle settlement separately. For example, each network can use a different central settlement bank where settlement accounts are established for participants in the network. In some embodiments, the first child network coordinator computer 550B can be associated with a financial institution that manages settlement accounts for each participant in the first child network 500B. Further, such a financial institution can establish its own settlement account for the parent network 500A at a higher central bank associated with parent network coordinator computer 550A. In other embodiments, a single central bank can manage accounts and settlements between all participants in two or more separate networks.

In order to further integrate the different networks, in some embodiments, all participants in all networks can register for participation with the parent network coordinator computer 550A. The parent network coordinator computer 550A can then issue globally unique enterprise identifiers for each registered participant. Alternatively, the parent network coordinator computer 550A can provide a set of unique enterprise identifiers to each child network coordinator, and the child network coordinators can then provide registration services and enterprise identifiers to participants.

As shown in FIG. 5, each network can maintain a separate record database. In some embodiments, each network can create records for transactions that take place within or involve that network. As a result different record databases can contain mostly different information, but can have some overlapping information related to cross-network transactions. In some embodiments, each network can build and maintain a separate blockchain ledger.

As mentioned above, embodiments allow the first child network coordinator computer 550B in FIG. 5 to be the same as or similar to the network coordinator computer 150 in FIG. 1. For example, similar to the network coordinator computer 150 in FIG. 1, the first child network coordinator computer 550B can comprise a processor, a network interface, any suitable databases, and a computer readable medium. Additionally, the computer readable medium may comprise code, executable by the processor, for implementing a method comprising receiving, from a node computer, a data package with first data, wherein the network coordinator computer and the node computer are associated with a first network; receiving a first digital signature associated with the first data, the first digital signature being generated with a first private key associated with the node computer; determining to transmit the data package to a second network; generating second data for the data package; generating a second digital signature for the second data, the second digital signature being generated using a second private key associated with the network coordinator computer; and transmitting, to the second network, the data package including the first data, the second data, the first digital signature, and the second digital signature.

Additionally, as mentioned above, embodiments also allow the parent network coordinator computer 550A in FIG. 5 to be the same as or similar to the network coordinator computer 150 in FIG. 1. For example, similar to the network coordinator computer 150 in FIG. 1, the parent network coordinator computer 550A can comprise a processor, a network interface, any suitable databases, and a computer readable medium. Additionally, the computer readable medium may comprise code, executable by the processor, for implementing a method comprising receiving, from a first network coordinator computer associated with a first network, a data package including first data and second data, a first digital signature, and a second digital signature, the first data having been generated by a node computer, the first digital signature having been generated by the node computer using a first private key and the first data, the second data having been generated by the first network coordinator computer, and the second digital signature having been generated by the first network coordinator computer using a second private key and the second data; generating third data for the data package; generating a third digital signature for the third data, the third digital signature being generated using a third private key associated with the second network coordinator computer; and transmitting, to a third network, the data package including the first data, the second data, the third data, the first digital signature, the second digital signature, and the third digital signature.

A method 600 according to embodiments of the invention can be described with respect to FIGS. 6A-6E. Some elements in other Figures are also referred to. The steps shown in the method 600 may be performed sequentially or in any suitable order in embodiments of the invention. In some embodiments, one or more of the steps may be optional.

The various messages described below may use any suitable form of communication. In some embodiments, a request or response may be in an electronic message format, such as an e-mail, a short messaging service (SMS) message, a multimedia messaging service (MMS) message, a hypertext transfer protocol (HTTP) request message, a transmission control protocol (TCP) packet, a web form submission. The request or response may be directed to any suitable location, such as an e-mail address, a telephone number, an Internet protocol (IP) address, or a uniform resource locator (URL). In some embodiments, a request or response may comprise a mix of different message types, such as both email and SMS messages.

At step S101, the first user computer 510 transmits a record request to the first child node computer 565. For example, the first user computer 510 in the first child network 500B can submit a request for sending a payment to the fifth user computer 513 in the second child network 500C. The record request can include the first user computer's enterprise identifier, the fifth user computer's enterprise identifier, and record update information for a specific record class.

In the payment transaction example, the record update information can comprise a type of currency to use as the payment source, a type of currency to deliver to the recipient, and an amount of currency to deliver to the recipient. For example, the first user may wish to send a payment of $1000 in Singapore dollars to the second user, but the first user may wish to make the payment from an account with US dollars.

At step S102, the first child node computer 565 determines a node associated with the fifth user computer 513, such that a data package with the interaction data can be addressed to that node. For example, in some embodiments, the first child node computer 565 can communicate with the first child network coordinator computer 550B to inquire about what node (e.g., the third child node computer 566) is associated with the second user computer's enterprise identifier, as well as to validate the second user computer's enterprise identifier. The first child network coordinator computer 550B may be able to identify the node locally, or may communicate with the parent network coordinator computer 550A to identify the node. In some embodiments, the first child node computer 565 can use a locally stored lookup table for identifying a node associated with the second user computer's enterprise identifier. In other embodiments, the first child node computer 565 can parse the second user computer's enterprise identifier to determine the second node computer's address identifier.

At step S103, the first child node computer 565 generates first data representing the interaction. The first data can be formatted as a data package that can be entered into a record. The first data can include any suitable information for describing the interaction. For example, the first data can include a sending currency amount and/or type, a destination currency amount and/or type, the first user computer's enterprise identifier, the fifth user computer's enterprise identifier, the first child node computer's address identifier, the third child node computer's address identifier, and/or any other suitable information.

At step S104, the first child node computer 565 generates a first digital signature associated with the first data in the data package. For example, the first child node computer 565 can generate a one-way hash using some or all of the first data, and then encrypt the hash using a private key (e.g., a first private key associated with the first child node computer 565). The hash data value and/or digital signature may be attached to the data package, thereby making the data package data-tampering evident.

In some embodiments, the data package can further include a transaction identifier. The first child node computer 565 can generate the transaction identifier and include the transaction identifier as part of the first data. Alternatively, the parent network coordinator computer 550A can generate unique transaction identifiers, and the first child node computer 565 or the first child network coordinator computer 550B can obtain a transaction identifier from the parent network coordinator computer 550A for the transaction.

At step S105, the first child node computer 565 transmits the data package with the first data and the first digital signature to the first child network coordinator computer 550B for validation and entering into a blockchain record.

At step S106, the first child network coordinator computer 550B can verify the first child node computer's digital signature and/or hash value. For example, the first child network coordinator computer 550B may perform a checksum procedure for the hash value. This can include generating a second hash value based on the data package and checking that the second hash value matches the received hash value. The first child network coordinator computer 550B may verify the digital signature using the first node computer's public key. The first child network coordinator computer 550B can reject the data package if the hash or digital signature cannot be verified.

At step S107, the first child network coordinator computer 550B can identify the intended recipient of the payment, which in this case can be the third child node computer 566 (e.g., as indicated by a recipient address identifier in the first data) and/or the fifth user computer 513 (e.g., as indicated by a recipient enterprise identifier in the first data). The first child network coordinator computer 550B can determine whether the recipient is a participant in the first child network 500B.

In this example, because the third child node computer is not a part of the first child network 500B, the first child network coordinator computer 550B can determine that the intended recipient is not within the first child network 500B. The first child network coordinator computer 550B can thereby determine that the interaction can be escalated to the parent network 500A.

In the case where the recipient is part of the first child network 500B, the first child network coordinator computer 550B can digitally sign the data package and transmit the data to the recipient. However, in the current example, the method can instead proceed to step S108.

At step S108, the first child network coordinator computer 550B can modify the data package to indicate that it is being escalated to the parent network 500A. This can include generating second data that describes that the indicated recipient is not within the initial network. In some embodiments, the second data can further indicate that funds will be first transferred to the first child network coordinator computer 550B, and then the funds will be transferred from the first parent node computer 551 in the parent network 500A to the originally intended third child node computer 566 or another intermediary (e.g., via two atomic transactions). Such information can be conveyed by providing the first child network coordinator computer's address identifier (and/or the first parent node computer's address identifier) and marking it as the new intermediary recipient. The second data can then be added to the data package.

At step S109, the first child network coordinator computer 550B can create a second digital signature for the second data. For example, the first child network coordinator computer 550B can generate a one-way hash using some or all of the second data, and then encrypt the hash using a private key (e.g., a second private key associated with the first child network coordinator computer 550B).

At step S110, the first child network coordinator computer 550B can add the data package to a record. For example, the first child network coordinator computer 550B can create a new block for a first child network 500B blockchain. The block can include the data package with the first data and the second data, as well as the associated digital signatures. The block can also include the transaction identifier for the transaction. The block may further include one or more additional data packages for other transactions.

At step S111, the first child network coordinator computer 550B can transmit the data package (e.g., with the first data and the second data) and the digital signatures to the parent network 500A. In some embodiments, this can include transmitting the data package to the first parent node computer 551. In other embodiments, this can include transmitting the data package to the parent network coordinator computer 550A.

At step S112, the first parent node computer 551 can transmit the data package and digital signatures to the parent network coordinator computer 550A. This step can function as the first parent node computer 551 submitting the data package as a new record entry in the parent network 500A. For example, step S112 can be similar to step S105, but with a modified data package and in a different network.

At step S113, the parent network coordinator computer 550A can verify one or both of the first digital signature and the second digital signature (and/or hash values). For example, the digital signatures can be verified using corresponding public keys. The parent network coordinator computer 550A can reject the data package if the hashes or digital signatures cannot be verified.

At step S114, the parent network coordinator computer 550A can determine that the third child node computer 566 and/or fifth user computer 513 are the intended recipients based on the first data and/or second data. Then, the parent network coordinator computer 550A can determine that the recipient is a participant in the second child network 500C. For example, the parent network coordinator computer 550A can maintain a lookup table with a complete list of enterprise identifiers and address identifiers, and the networks with which they are associated. Accordingly, the parent network coordinator computer 550A can determine that the transaction can be routed to the second child network 500C. This can be done by providing the data package to the second parent node computer 552 in the parent network 500A, because the second parent node computer 552 may be able to communicate with the second child network 500C.

At step S115, the parent network coordinator computer 550A can further modify the data package to indicate that it is being routed to the second child network 500C. This can include generating third data that describes that the indicated recipient is not within the parent network 500A. In some embodiments, the third data can further update the details of the transaction. The third data can specify that the transfer path of the funds will now be from the first child node computer 565 to the first child network coordinator computer 550B within the first child network 500B, then from the first parent node computer 551 to the second parent node computer 552 within the parent network 500A, and then from the second child network coordinator computer 550C to the to the originally intended third child node computer 566 within the second child network 500C. Thus, the third data can specify three atomic transactions within three networks that can, in combination, achieve the originally intended transaction from the first child node computer 565 (on behalf of the first user computer 510) to the third child node computer 566 (on behalf of the fifth user computer 513). The third data can include enterprise identifiers and/or address identifiers for each entity, as well as any other suitable information for describing the updated transaction details. The third data can then be added to the data package.

At step S116, the parent network coordinator computer 550A can create a third digital signature for the third data. For example, the parent network coordinator computer 550A can generate a one-way hash using some or all of the third data, and then encrypt the hash using a private key (e.g., a third private key associated with the parent network coordinator computer 550A).

At step S117, the parent network coordinator computer 550A can add the data package to a new record. For example, the parent network coordinator computer 550A can create a new block for a parent network 500A blockchain. The block can include the data package with the first data, the second data, the third data, and also the associated digital signatures. The block can also include the transaction identifier. The block may also include one or more additional data packages for other transactions. Thus, this can be the second block storing information about the transaction, and the block may be in a second, separate blockchain. Additionally, the same transaction can be identified within the two separate blockchains based on the same transaction identifier.

At step S118, the parent network coordinator computer 550A can transmit the data package (e.g., with the first data, the second data, and the third data) and the digital signatures to the second parent node computer 552. In other embodiments, the parent network coordinator computer 550A can transmit the data package directly to the second child network coordinator computer 550C.

At step S119, the second parent node computer 552 can transmit the data package and digital signatures to the second child network coordinator computer 550C in the second child network 500C. This step can effectively function as the second parent node computer 552 submitting the data package as a new record entry for the second child network 500C. For example, step S119 can be similar to step S105, but with a modified data package, in a different network, and as a cross-network communication.

At step S120, the second child network coordinator computer 550C can verify one, two, or all three of the digital signatures (and/or hash values). For example, the digital signatures can be verified using corresponding public keys. The second child network coordinator computer 550C can reject the data package if the hashes or digital signatures cannot be verified.

At step S121, the second child network coordinator computer 550C can determine that the third child node computer 566 and/or fifth user computer 513 are the intended recipients based on the first data, second data, and/or third data. Then, the second child network coordinator computer 550C can determine that the recipient is a participant in the second child network 500C. Accordingly, the second child network coordinator computer 550C can determine that the transaction can be completed within the second child network 500C, and that no additional modifications to the data package or transfers to other networks are necessary.

At step S122, the second child network coordinator computer 550C can create a fourth digital signature for the data package. For example, the second child network coordinator computer 550C can generate a one-way hash using some or all of the first data, second data, and/or third data, and then encrypt the hash using a private key (e.g., a fourth private key associated with the second child network coordinator computer 550C).

At step S123, the second child network coordinator computer 550C can add the data package to a new record. For example, the second child network coordinator computer 550C can create a new block for a second child network 500C blockchain. The block can include the data package with the first data, the second data, the third data, and also the associated digital signatures. The block can also include the transaction identifier. The block may also include one or more additional data packages for other transactions. Thus, this can be the third block storing information about the transaction, and the block may be in a third, separate blockchain. Additionally, the same transaction can be identified within three separate blockchains based on the same transaction identifier.

At step S124, the second child network coordinator computer 550C can transmit a copy of the data package and/or the digital signatures to the third child node computer 566 (e.g., to inform the third child node computer 566 about the transaction). The second child network coordinator computer 550C can also make the blockchain record accessible to the third child node computer 566.

At step S125, the third child node computer 566 can verify the authenticity of the data package. For example, the third child node computer 566 can confirm that the data package has been entered into a blockchain record (e.g., by accessing the blockchain record at the second child network coordinator computer 550C). The third child node computer 566 can also verify that the data package includes digital signatures for each portion of data in the data package (e.g., the first data, the second data, and the third data). The third child node computer 566 can also verify one or more of the digital signatures (e.g., using the appropriate public keys). All of these verifications, in combination, can create a high-level of trust in the authenticity of the data package, as well as a high-level of trust that a promised interaction will be completed.

At step S126, the third child node computer 566 can update its local records based on the data package. For example, the third child node computer 566 can credit the promised transaction value (e.g., as indicated in the data package) to the fifth user's bank account. Because there may be a high-level of trust in the interaction, the third child node computer 566 may credit the fifth user's account so that the funds can be withdrawn before the transaction value is actually settled.

At a later time, steps can be taken to settle each atomic transaction indicated in the data package. One or more of the network coordinator computers may send instructions (e.g., the data package) to one or more central banks, such that the one or more central banks can execute settlements. In some embodiments, central bank computers can access records (e.g., blockchain ledgers) maintained by the network coordinator computers, and can analyze the records to determine what settlement transactions to complete. The central bank computers can review the instructions and/or data package to determine each scheduled atomic payment transaction that is to be completed.

At step S127, one or more interactions can be performed based on the package. For example, a first central bank computer associated with the first child network 500B can cause a transfer of funds from a first child node account to a first child network coordinator account at a first central bank, according to the first atomic transaction specified by the data package. Then, a second central bank computer associated with the parent network 500A can cause a transfer of funds from a first parent node account to a second parent node account at a second central bank, according to the second atomic transaction specified by the data package. Then, a third central bank computer associated with the second child network 500C can cause a transfer of funds from a second child network coordinator account to a third child node account at a third central bank, according to the third atomic transaction specified by the data package. Embodiments allow net settlement, batch settlement, and/or multilateral network settlement techniques to be utilized.

In other embodiments, instead of three separate atomic transactions, the funds can be transferred directly from a first child node account to a third child node account. For example, both the first child node and third child node can establish accounts at the same central bank, and the value can be transferred between these accounts by the central bank. The data package can be transferred through the other entities and networks, as described above, but the settlement can take place directly between the two accounts.

Embodiments of the invention have a number of advantages. For example, in embodiments of the invention, separate networks can become interactive and interoperable through a connecting parent network. Coordinating entities for child networks can interact with the parent network as nodes in the parent network, and can thereby transmit data packages from one network to another. This advantageously unites the networks so that data packages can be sent globally, instead of just within one network. Further, a central parent network can provide globally unique identifiers for participants in the child networks.

Additionally, embodiments advantageously refrain from requiring all participants to adhere to a single global network. By maintaining separate networks, it is possible to maintain some privacy. For example, individual child networks can create a local blockchain ledger, and may not share the contents of the ledger outside of the network. Additionally, local child networks can use specialized rules and procedures. Further, a system with multiple networks allows record processing to be distributed among several different coordinating computers, thereby easing the processing burden and improving processing speed and efficiency. Accordingly, embodiments provide the benefits of a unified global network, such as a global reach and unique identifiers, while maintaining the benefits of separate local networks, such as privacy and efficiency.

A computer system will now be described that may be used to implement any of the entities or components described herein. Subsystems in the computer system are interconnected via a system bus. Additional subsystems include a printer, a keyboard, a fixed disk, and a monitor which can be coupled to a display adapter. Peripherals and input/output (I/O) devices, which can couple to an I/O controller, can be connected to the computer system by any number of means known in the art, such as a serial port. For example, a serial port or external interface can be used to connect the computer apparatus to a wide area network such as the Internet, a mouse input device, or a scanner. The interconnection via system bus allows the central processor to communicate with each subsystem and to control the execution of instructions from system memory or the fixed disk, as well as the exchange of information between subsystems. The system memory and/or the fixed disk may embody a computer-readable medium.

As described, the inventive service may involve implementing one or more functions, processes, operations or method steps. In some embodiments, the functions, processes, operations or method steps may be implemented as a result of the execution of a set of instructions or software code by a suitably-programmed computing device, microprocessor, data processor, or the like. The set of instructions or software code may be stored in a memory or other form of data storage element which is accessed by the computing device, microprocessor, etc. In other embodiments, the functions, processes, operations or method steps may be implemented by firmware or a dedicated processor, integrated circuit, etc.

Any of the software components or functions described in this application may be implemented as software code to be executed by a processor using any suitable computer language such as, for example, Java, C++ or Perl using, for example, conventional or object-oriented techniques. The software code may be stored as a series of instructions, or commands on a computer-readable medium, such as a random access memory (RAM), a read-only memory (ROM), a magnetic medium such as a hard-drive or a floppy disk, or an optical medium such as a CD-ROM. Any such computer-readable medium may reside on or within a single computational apparatus, and may be present on or within different computational apparatuses within a system or network.

While certain exemplary embodiments have been described in detail and shown in the accompanying drawings, it is to be understood that such embodiments are merely illustrative of and not intended to be restrictive of the broad invention, and that this invention is not to be limited to the specific arrangements and constructions shown and described, since various other modifications may occur to those with ordinary skill in the art.

As used herein, the use of "a", "an" or "the" is intended to mean "at least one", unless specifically indicated to the contrary.

What is claimed is:

1. A method comprising:
receiving, by a network coordinator computer, from a first node computer, a data package including first data and a transaction identifier, wherein the network coordinator computer and the first node computer are associated with a first network, wherein the first data describes an interaction between the first node computer and a second node computer;
determining, by the network coordinator computer, based on the first data, that the interaction is associated with the second node computer, and that the second node computer is not associated with the first network, wherein the second node computer is associated with a third network;
in response to determining that the second node computer is not associated with the first network, determining to transmit the data package to a second network;
modifying, by the network coordinator computer, the data package to further include second data, wherein the second data includes a modification to the interaction;
generating, by the network coordinator computer, a first block for a first blockchain associated with the first network, the first block including the data package with the first data, the second data, and the transaction identifier; and
transmitting, by the network coordinator computer, to the second network, the data package including the first data and the second data, wherein a second block is generated for a second blockchain associated with the second network, the second block including the data package with the first data, the second data, and the transaction identifier, wherein the data package is further modified to include third data at the second network, the third data including an additional modification to the interaction, wherein the second block includes the third data, and wherein the data package is subsequently transmitted from the second network to the third network.

2. The method of claim 1, wherein a third block is generated for a third blockchain associated with the third network, the third block including the data package with the first data, the second data, and the third data.

3. The method of claim 1, further comprising:
receiving, by the network coordinator computer, a first digital signature associated with the first data, the first digital signature being generated with a first private key associated with the first node computer, wherein the data package further includes the first digital signature; and generating, by the network coordinator computer, a second digital signature for the second data, the second digital signature being generated using a second private key associated with the network coordinator computer, wherein modifying the data package further includes adding the second digital signature to the data package, wherein a third digital signature is generated for the third data at the second network, the data package is further modified at the second network to include third digital signature, the first block further includes the first digital signature and the second digital signature, and the second block further includes the first digital signature, the second digital signature, and the third digital signature.

4. The method of claim 3, further comprising:
verifying, by the network coordinator computer, the first digital signature using a first public key associated with the first node computer, wherein the second digital signature is verified at the second network using a second public key associated with the network coordinator computer.

5. A method comprising:
receiving, by a second network coordinator computer associated with a second network, a data package including first data, second data, and a transaction identifier, wherein the first data is provided by a first node computer associated with a first network, the second data is provided by a first network coordinator computer associated with the first network, the first data describes an interaction between the first node computer and a second node computer, the second data includes a modification to the interaction, and the first network coordinator computer generates a first block for a first blockchain associated with the first network, the first block including the data package with the first data, the second data, and the transaction identifier;
determining, by the second network coordinator computer, based on at least one of the first data and the second data, that the interaction is associated with the second node computer, and that the second node computer is associated with a third network;
in response to determining that the second node computer is associated with the third network, determining to transmit the data package to the third network;
modifying, by the second network coordinator computer, the data package to further include third data, wherein the third data includes an additional modification to the interaction;
generating, by the second network coordinator computer, a second block for a second blockchain associated with the second network, the second block including the data package with the first data, the second data, the third data, and the transaction identifier; and
transmitting, by the second network coordinator computer, to the third network, the data package including the first data, the second data, the third data, and the transaction identifier.

6. The method of claim 5, wherein, when the data package is received from the first network coordinator computer associated with the first network, the data package further includes a first digital signature generated by the first node computer using a first private key and the first data, and a second digital signature generated by the first network coordinator computer using a second private key and the second data, and the method further comprising:
generating, by the second network coordinator computer, a third digital signature for the third data, the third digital signature being generated using a third private key associated with the second network coordinator computer, wherein modifying the data package further includes adding the third digital signature to the data package.

7. The method of claim 6, further comprising:
verifying, by the second network coordinator computer, the first digital signature using a first public key associated with the first node computer or the second digital signature using a second public key associated with the first network coordinator computer, and wherein at least one of the first digital signature, the second digital signature, and the third digital signature are verified at the third network.

8. The method of claim 6, wherein the data package is provided to the second node computer.

9. The method of claim 5, wherein the first network coordinator computer determined that the second node computer is an indicated recipient of the data package, determined that the second node computer is not within the first network, and determined to transmit the data package to the second network.

10. The method of claim 5, wherein the first network coordinator computer modified the data package to include the second data.

11. The method of claim 5, wherein a third block is generated for a third blockchain associated with the third network, the third block including the data package with the first data, the second data, and the third data.

12. The method of claim 5, wherein the second network is a parent network, and wherein the first network and the third network are child networks of the second network.

13. The method of claim 5, wherein the second data describes that an indicated recipient of the data package is not within the first network.

14. A method comprising:
receiving, by a third network coordinator computer associated with a third network, a data package including first data, second data, third data, and a transaction identifier, wherein the first data is provided by a first node computer associated with a first network, the second data is provided by a first network coordinator computer, the third data is provided by a second network coordinator computer associated with a second network, the first data describes an interaction between the first node computer and a second node computer, the second data includes a modification to the interaction, the third data includes an additional modification to the interaction, the first network coordinator computer, determines that the interaction is associated with the second node computer, that the second node computer is not associated with the first network, and that the second node computer is associated with the third network, the first network coordinator computer determines to transmit the data package to the second network, the first network coordinator computer generates a first block for a first blockchain associated with the first network, the first block including the first data, the second data and the transaction identifier, and the second network coordinator computer generates a second block for a second blockchain associated with the second network, the second block including the first data, the second data, the third data, and the transaction identifier; and generating, by the third network coordinator computer, a third block for a third blockchain associated with the third network, the third block including the data package with the first data, the second data, and the third data, and the transaction identifier.

15. The method of claim 14, further comprising:
providing the data package to the second node computer.

16. The method of claim 14, wherein the data package further includes a first digital signature generated by the first node computer using a first private key and the first data, a second digital signature generated by the first network coordinator computer using a second private key and the second data, and a third digital signature generated by the second network coordinator computer using a third private key and the third data, and the method further comprising:
verifying:
(a) the first digital signature using a first public key associated with the first node computer, or
(b) the second digital signature using a second public key associated with the first network coordinator computer, or
(c) the third digital signature using a third public key associated with the second network coordinator computer.

* * * * *